United States Patent [19]

Jackson et al.

[11] Patent Number: 5,372,033
[45] Date of Patent: Dec. 13, 1994

[54] EHL TEST MACHINE FOR MEASURING LUBRICANT FILM THICKNESS AND TRACTION

[75] Inventors: Andrew Jackson, Pennington, N.J.; Andries Kuivenhoven, London Yard, United Kingdom; Martin N. Webster, Pennington, N.J.

[73] Assignee: Mobil Oil Corporation, Fairfax, Va.

[21] Appl. No.: 154,056

[22] Filed: Nov. 18, 1993

[51] Int. Cl.⁵ .................................. G01N 33/30
[52] U.S. Cl. ........................... 73/53.05; 73/10
[58] Field of Search ....................... 73/53.05, 10

[56] References Cited

U.S. PATENT DOCUMENTS

| | | | |
|---|---|---|---|
| 2,808,563 | 10/1957 | Hornbostel | 73/10 X |
| 2,883,855 | 4/1959 | Spengler et al. | 73/53.05 X |
| 3,178,928 | 4/1965 | Howe | 73/9 |
| 3,785,196 | 1/1974 | Smith | 73/53.05 |
| 3,952,566 | 4/1976 | Jacobson | 73/10 |
| 4,000,656 | 4/1977 | Moioli | 73/53.05 X |
| 4,253,326 | 3/1981 | Munnich et al. | 73/10 |
| 4,263,374 | 4/1981 | Glass et al. | 428/693 |
| 4,443,754 | 4/1984 | King | 73/53.05 X |
| 4,854,159 | 8/1989 | Bates | 73/53.05 |
| 5,001,435 | 3/1991 | Smith | 73/53.05 |

Primary Examiner—Thomas P. Noland
Assistant Examiner—Joseph W. Roskos
Attorney, Agent, or Firm—Alexander J. McKillop; George W. Hager, Jr.; Charles A. Malone

[57] ABSTRACT

A method and apparatus for measuring thickness and traction properties of elastohydrodynamic lubricant (EHL) films is described. The apparatus utilizes at least one ball or roller loaded against the internal diameter of a transparent ring having a larger radius than said ball or roller. A lubricant is placed between the rotating roller and ring thereby forming an EHL film where the ball and ring contact. Roller and ring rotating speeds are controlled to obtain different amounts of relative sliding motion between their surfaces. Contact between the surfaces and the resultant film are observed via the transparent ring which allows optical measurements of lubricating film thickness. Traction forces generated during contact are measured by any suitable force measuring device.

44 Claims, 5 Drawing Sheets

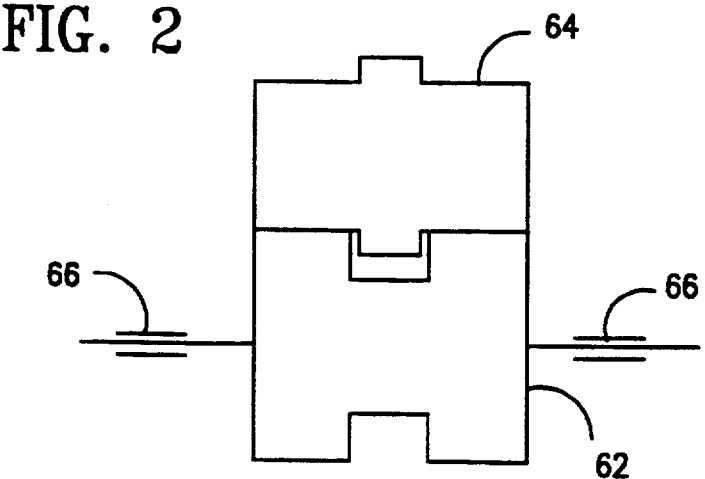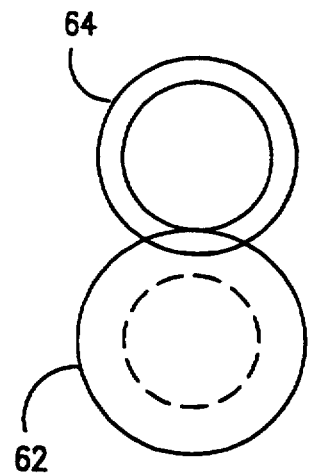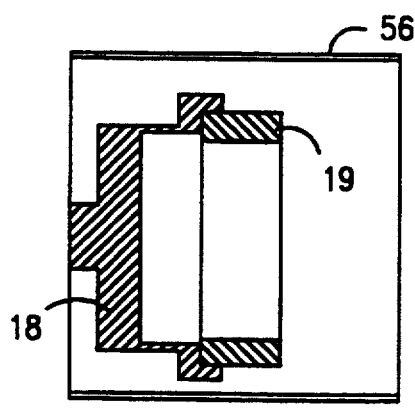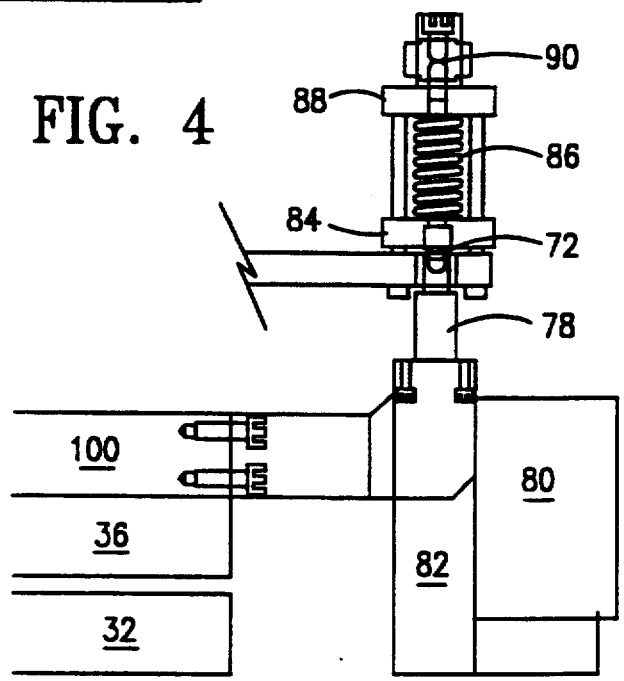

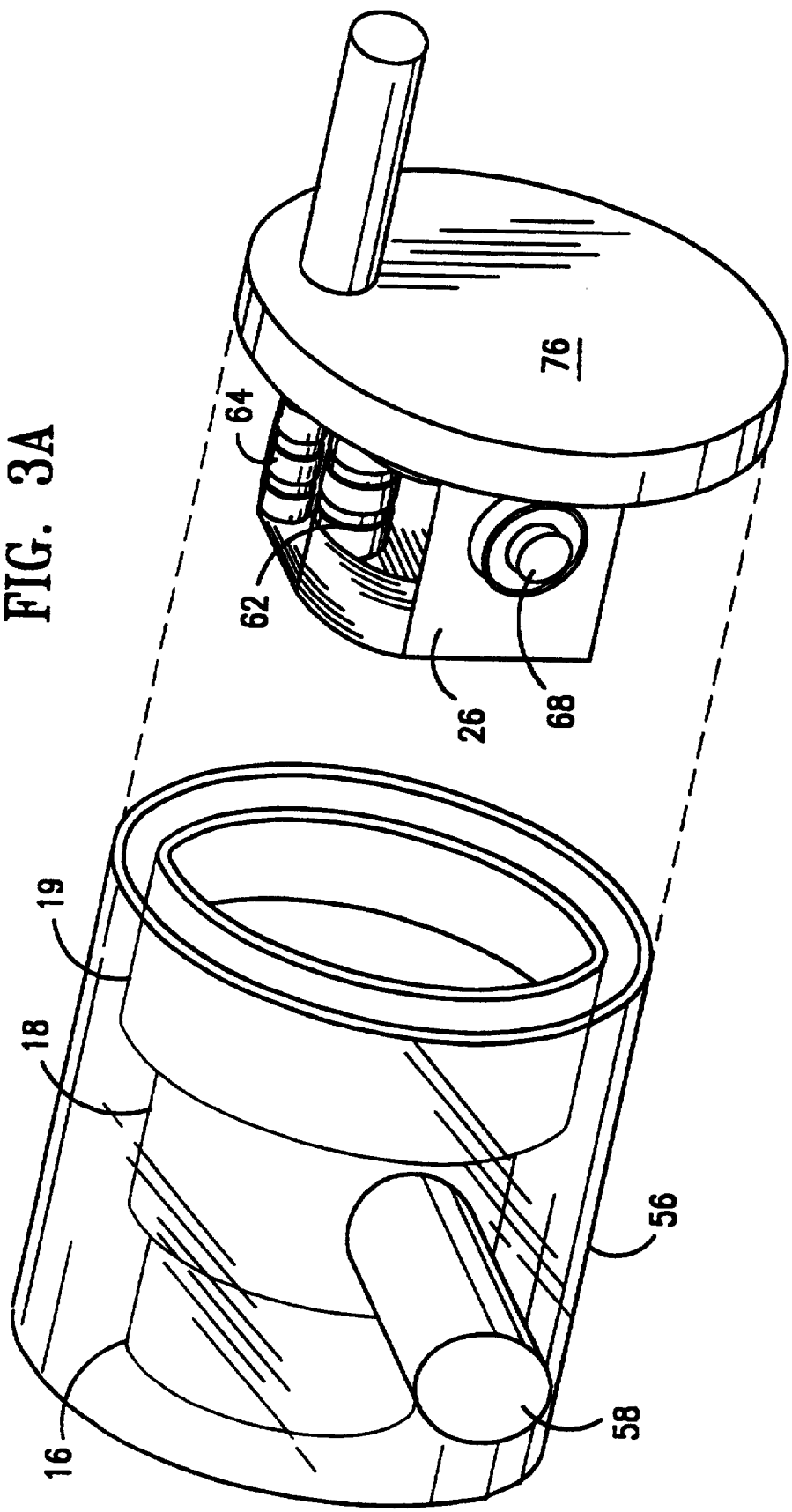

EHL TEST MACHINE FOR MEASURING LUBRICANT FILM THICKNESS AND TRACTION

FIELD OF THE INVENTION

This invention relates to methods and apparatuses for measuring the thickness and traction properties of elastohydrodynamic lubricant (EHL) films. More specifically, traction forces generated by contacting lubricants with components of the apparatus are measured.

BACKGROUND OF THE INVENTION

In the prior art, it has long been recognized that the proper generation and maintenance of the lubricant film between the rolling elements and races of an operating rolling element bearing assembly and between meshing gear teeth are critical with respect to bearing and gear life and maintainability. As a consequence, there have been many attempts in the prior art to measure elastohydrodynamic lubricant film thickness in actual bearings or in apparatus in which the bearings or gears are simulated. Some of these measurement schemes have involved the electrical measurement of resistance, of dielectric breakdown voltage, or of the effective capacitance of the lubricant film under operating conditions. In addition, x-ray diffraction techniques and optical interferometric methods have been applied with certain degrees of success.

Because of their nature, most of the prior art test arrangements have involved specially prepared and instrumented bearing assemblies which usually do not allow detailed study of a lubricant's behavior under conditions typically found in gear and rolling element bearing contacts. One such example of a test device involving bearing simulation is taught in U.S. Pat. No. 3,178,928, issued on Apr. 20, 1965 to T. B. Howe, and assigned to Sperry Rand Corporation. In the Howe apparatus, important characteristics of ball bearings or elements thereof may be investigated by a simulation method so that valuable data may be obtained through measurements of torque and electrical resistance, the measurements providing an indication of operation efficiency. Since the apparatus is a simulation apparatus, interchangeability of simulated bearing components is permitted to some extent. The device provides output data respective to the torque transmitted through the ball elements as well as the electrical resistance to currents passing through the lubricating film associated with those ball elements. Changes in efficiency of the simulated bearing are generally indicated by rising or erratic torque or electrical resistance indications that can be used to predict failure well in advance of the failure event.

However, like many of the prior art test concepts, studies using the Howe apparatus are performed on simulated bearing arrangements and the concept does not readily permit the direct testing of commercially produced bearings or the testing of lubricants directly in such commercial bearings.

The reliability and life of a ball bearing is a function of its lubricating film thickness with respect to minute irregularities in the surface finish of the bearing balls and races. The film thickness of consequence is that of the plateau at the central contact locus of the lubricating film. The trailing edge of this separating film is reduced in thickness by the hydraulic, elastic, hydrodynamic, and other forces involved. It has been determined experimentally that bearing life is most closely associated with the lubrication film thickness in the central plateau region and is not significantly related to that at the exit region restriction which is normally measured by electrical resistance measurements. Thus, electrical resistance measurements, while useful for many purposes, are often not as accurate an indicator of bearing life as is desired. Furthermore, it is not possible to search a bearing race for local imperfections, such as for areas in which a sufficient lubrication film does not exist due to an oleophobic surface, misalignments, or local raceway surface defects.

It is recognized that ultrasonic energy has been employed in the past for various testing purposes, such as, for example, the detection of hidden flaws deep within solid structures. In such conventional ultrasound test equipment, for example, a pulse of energy is directed through a medium toward a defect or other interface and the arrival time of the reflected wave at a receiver is measured in order to afford a measurement of the depth of the flaw or other interface. However, the technique lends itself to use only in situations in which the flaw or interface to be observed is buried relatively deeply within the medium. Thus, the direct measurement of films as thin as bearing lubrication films would not prove to be practical using this conventional technique.

Jacobson in U.S. Pat. No. 3,952,566 discloses a method and apparatus where a bearing and elastohydrodynamic lubrication film are measured by relating acoustic resonance frequencies of a ball raceway lubricant system of a ball bearing, which frequencies are found to be related to bearing ball, race, and lubricant behavior. These measurements are made while the bearing is actually operating in its normal environment such as for example in a production gyroscopic instrument assembly.

Previous configurations as mentioned above consist of either balls or rollers loaded against a flat face of a disc of alternatively a number of discs forming an external contact on their circumferences. Use of ball or roller on disc configurations limit the speed at which measurements can be made due to centrifugal forces experienced by the lubricant. At high speeds lubricant is forced away from metal contact which contact becomes starved of lubricant. External contact of discs allows high speed traction measurements but it is difficult to view the contact directly using optics.

Therefore, what is needed is a method and apparatus which eliminates lubricant starvation due to centrifugal forces while allowing direct measurement of traction and optical film thickness measurements to be made under EHL conditions.

SUMMARY OF THE INVENTION

In the practice of this invention, a lubricant to be tested is placed onto a rolling element and dispersed thereon. This rolling element is affixed to a rotatable shaft. This shaft is connected to a means for rotating the shaft and transmitting power to vary the speed of the roller via said shaft. The roller is positioned so as to enable contact inside an independently rotatable ring. Power is transmitted to the shaft thus causing the roller to rotate at a desired speed while contact is made with the rotating ring. A desired load is placed on the roller via a loading assembly means. As the roller rotates, an elastohydrodynamic lubricant (EHL) film to be generated between the roller and ring. If a transparent ring is used, this film is visible through the ring and creates an interference pattern detectable through said ring.

Traction forces generated by the EHL film as it enters between the rotating roller and ring are transmitted from the roller through a test roller support and assembly to force cells which change the forces into electrical signals which are directed to force transducers. A traction force transducer is positioned so as to measure forces transmitted from the rotating roller and ring affixed to the ring assembly. Side forces caused by the rotating roller and ring are transmitted to a side force transducer that is attached to the moveable base which supports the ring assembly to a fixed base. A load is applied to the roller by a loading assembly which is positioned above a moveable base plate with a frictionless pad therebetween. By varying the load on the roller and speeds on the independently rotating roller and ring, traction measurements can be obtained over a wide range of contact pressures along with varying film thickness measurements. These obtained traction and film measurements can be used to tailor lubricants to fit required operating conditions e.g. energy conservation, fuel economy, and power transfer.

It is therefore an object of this invention to optically measure film thickness under EHL conditions.

It is another object of this invention to measure lubricant traction properties under EHL conditions.

It is further object of this invention to provide a machine which can generate film thickness and traction data over a broad range of loads, speeds and temperatures.

BRIEF DESCRIPTION OF THE DRAWINGS

FIG. 2 is a side view of a roller that is being supported by one support roller.

FIG. 2A is a frontal view of a single roller being supported by a support roller.

FIG. 3 is a cross-sectional view of a ring assembly with a transparent ring located therein which assembly is surrounded by a transparent housing means.

FIG. 3A is a topical view of a single roller being supported by two support rollers where the roller support assembly has a circumferential metal lid placed therearound where the transparent housing means surrounds the sapphire ring.

FIG. 4 is a cross-sectional view of the loading assembly affixed to a moveable plate with a frictionless pad located above the fixed plate.

DESCRIPTION OF THE PREFERRED EMBODIMENTS

Figure 1:
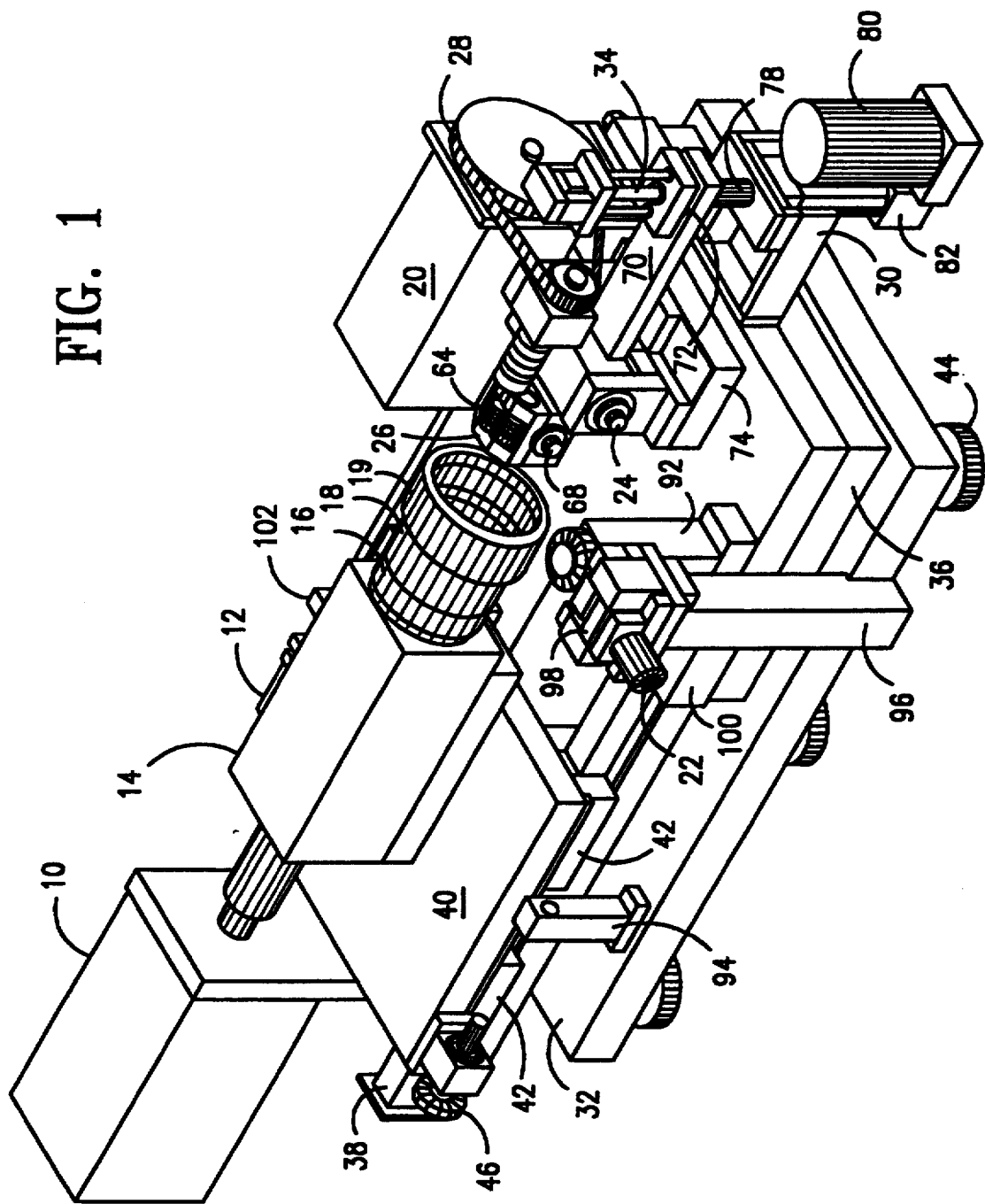
FIG. 1 is an overview of the EHL machine.

In the practice of this invention referring to FIG. 1, a lubricant is placed onto roller 64 which forms a part of test roller support assembly 26. This roller support assembly is shown in greater detail in FIG. 2. As shown in FIG. 2, roller 64 is an elongated cylinder of about ½ of an inch in diameter. Depressions are contained in this rollers so as to conform to raised circumferential ridges on support rollers 62 therearound. Centrally located in roller's 64 anterior end is a shaft of about 1½ inches long, which also represents the length of the roller. The roller shaft is used to couple the roller to a belt drive 28 for the transmission of power from roller drive servo 20 shown in FIG. 1. Servo 20 is a brushless servo-motor which can be purchased from Pacific Scientific in Rockford, Ill.

Positioned below roller 64 are two support rollers 62. These support rollers 62 contain centrally located shafts at their anterior and posterior ends which ends each contain roller support bearings 66 therearound. Bearings 66 are held in place in roller support assembly 26 which is preferably made of metal. Support rollers 62 are positioned below roller 64. Preferably, roller 64 has two raised circumferentially surfaces, one at each end of roller 64. These raised surfaces fit within corresponding depressions in support rollers 62. As is shown in FIG. 2, one circumferential surface can be used. Roller pivotal shaft 68 passes through the side of roller support assembly 26 where it is located below and perpendicular to support rollers 62. Roller support assembly 26 is fixably attached to the shorter end of loading arm 70. Loading arm 70 contains a raised portion adaptably fitted to receive a fulcrumed shaft perpendicularly across arm 70. As shown in FIG. 1, the longest end of loading arm 70 is fitted to receive v-shaped knife edge 72 for applying a loading force onto arm 70.

When a load is applied to knife edge 72, a loading force is transmitted downwardly thereon causing it to pivot on roller pivotal shaft 68 which forces roller test assembly 26 upwardly. As roller pivotal shaft 68 passes through loading arm 70, each end of shaft 68 is located in pivotal shaft support 74 which is fixably attached to moveable frictionless pad 36. Frictionless pad 36 is supported by fixed base plate 32 containing base levelers therebelow. Fixed base plate 32 is preferentially made of cast iron. An adjustable leg means 44 can be used to balance fixed base plate 32.

Figure 3B:
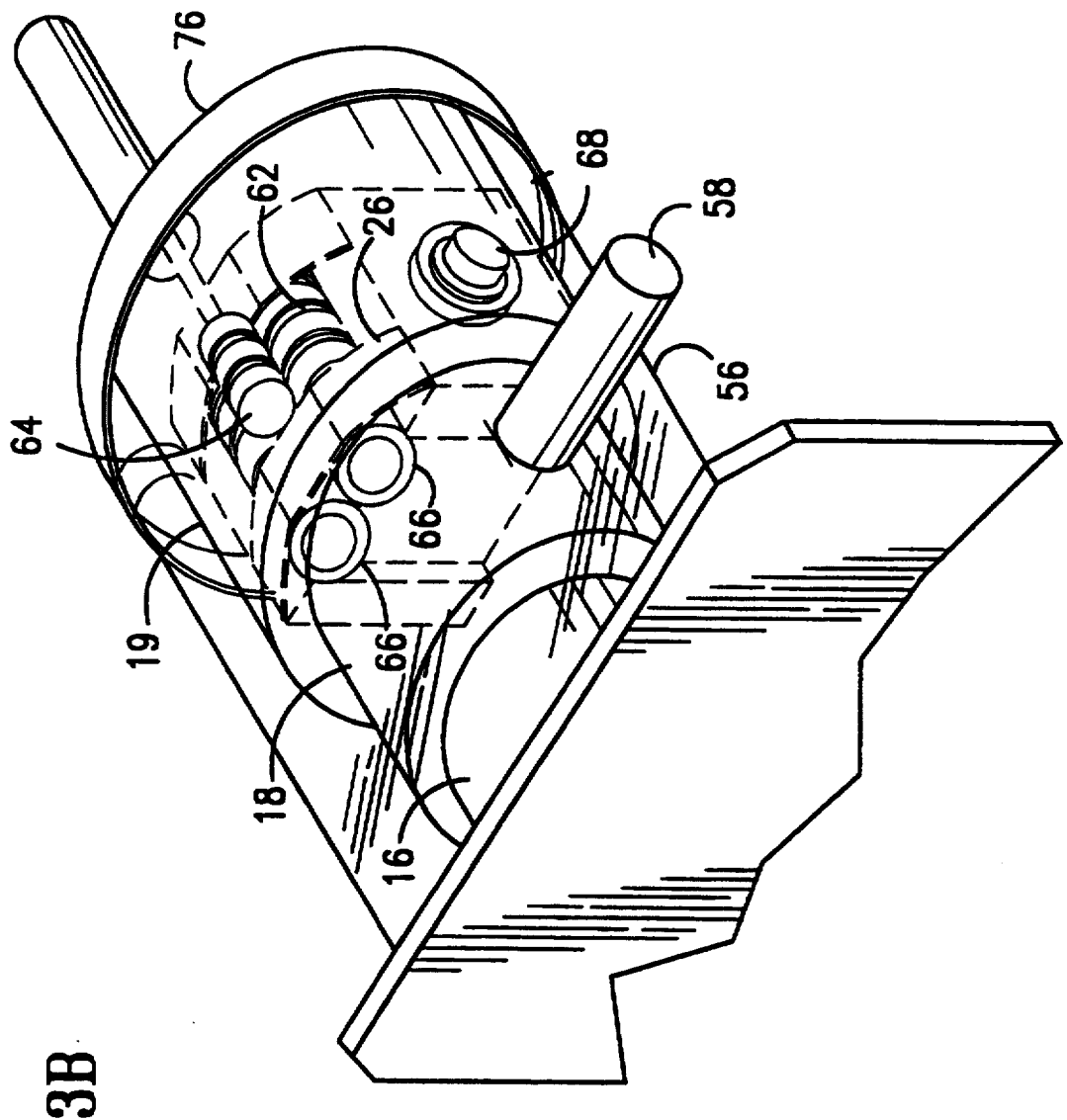
FIG. 3B is a topical view of a single roller being supported by two support rollers where the circumferential metal lid around the roller support assembly is inside the sapphire ring and the transparent housing means surrounding the ring is engaged with the lid to form a heating or cooling chamber.

Roller support assembly 26 is positioned into a metal lid 76, as shown in FIGS. 3A and 3B, which lid receives therein a transparent cylindrical housing means 56 that fits around ring assembly 18 so as to form a closed heating or cooling means when ring assembly 18 is engaged over roller support assembly 26. The end of cylindrical housing means 56 which fits over roller support assembly 26 is open while its opposite end is closed but contains centrally located opening therein so as to allow a shaft affixed to ring assembly 18 to pass therethrough. The closed end is supported on spindle/ring positioning mechanism 40 which is movable along rail guide 42 positioned therebelow. Rail guides 42 are fittingly affixed to fixed base plate 32, as shown in FIG. 1.

After having placed the lubricant on roller 64, ring assembly 18 with a sapphire ring affixed therein is moved horizontally by means of the rail guides so as to fit over roller support assembly 26. This is shown in FIG. 3. Positioned in this manner, roller 64 contacts the inside of the sapphire ring 19 affixed to ring assembly 18 while metal lid 76 fits over transparent housing means 56. Thus, ring assembly 18 and roller support assembly 26 are enclosed by transparent housing means 56 and metal lid 76 thereby providing a chamber or enclosure means for circulating heated or cooled air around ring assembly 18 and roller support assembly 26. Preferably, this chamber or enclosure means is made of a transparent plastic material.

Although the ring utilized is made of sapphire, it and the roller can be made from other materials if it is only desired to make traction measurements. Examples of the material from which the ring and roller can be made include steel, bronze, tungsten carbide, and ceramic materials, or combinations and mixtures thereof.

In order to accurately position and hold the ring and roller in contact with each other, positioning screw spindle 46 is engaged by screwing it into positioning screw spindle holder 94. When the ring and roller are not engaged, screw spindle 46 is disengaged, thus, allowing free movement of the spindle ring assembly on positioning rails 38.

Once ring assembly 18 and roller support assembly 26 are within the enclosure formed by metal lid 76 and transparent housing means 56, cooled or heated air is directed into an opening in the side of transparent cylindrical housing means 56 via heater hose 58 as shown in FIG. 3B. Air is directed into this enclosure for a time sufficient to heat or cool the sapphire ring in ring assembly 18 and roller in roller support assembly 26 to a desired temperature. The enclosure with ring assembly 18 and roller support assembly 26 are shown in FIGS. 3A and 3B. Preferably, this temperature will be from about −20° C. to about 120° C. depending on a desired test protocol. Air is continually directed into cylindrical housing means 56 to maintain a desired temperature. A thermocouple is used to detect the temperature in the enclosure and is positioned so as to fit within the housing 56. Once the desired temperature is obtained, a load is placed onto loading arm 70 which load is transferred to roller 64 and the sapphire ring. Prior to loading arm 70, ring assembly 18 and roller support assembly 26 are aligned along its X and Y axis to relieve and balance stress forces.

A load ranging from about 10 lbs. to about 300 lbs. is placed on arm 70 via knife edge 72. The preferred means of loading arm 70 is by applying a loading force to knife edge 72 by loading jack 78 which is gearably connected to brushless servo motor 80. Loading jack 78 passes through an opening in loading assembly 30 which is fittingly attached to frictionless pad 36. Loading jack 78 extends through a retainer support means 82 which remains stationary as shown in FIG. 4. The loading jack also extends through a first spring retainer 84, spring 86, and a second spring retainer 88. The uppermost end of loading jack 78 is connected to load cell 90 for measuring the load which is applied.

Loading jack 78 when activated by loading servomotor 80, pulls the second spring retainer down thus compressing spring 86 onto spring retainer 84 and applying a desired load through knife edge 72 onto loading arm 70 and to roller 64 via roller support assembly 26. Once a desired Load is obtained, the desired load is maintained until the test protocol is terminated.

After loading roller 64, ring drive servo 10 is activated causing a shaft coupled with spindle unit 14 to rotate ring assembly 18 to a desired speed, which will be from about 500 to about 3,000 rpm. As ring assembly 18 rotates, it rotates the sapphire ring attached thereto against roller 64. A lubricant film is deposited on the ring between roller 64. While the ring is rotating at a speed of about 1,000 rpm for example, roller drive servo 20 is activated causing belt drive 28 to rotate a shaft fixably attached to the shaft on the anterior end of roller 64. Roller 64 is rotated at a speed slower than the rotating ring. The roller will rotate e.g. at a speed of 500 rpm. As roller 64 rotates, rotating motion therefrom transfers to roller supports 62 causing them to "free wheel" within roller support bearings 64 located in roller support assembly 26.

While the ring and roller 64 are rotating a lubricant film forms along the line contact made between the ring and roller 64. This film is visible through the transparent sapphire ring. A Wild Heerburg microscope supported on base plate 32 is slideably affixed to a moveable microscope adjusting means which enables the microscope to be positioned above the ring area where the film is visible. By the use of optical interference or interferometry, EHL film thickness is determined. A method for making this determination for low-loss ferrite films is discussed in U.S. Pat. No. 4,263,374 which issued to H. L. Glass et al. on May 26, 1981. This patent is hereby incorporated by reference herein.

While the ring and roller continue to rotate EHL traction forces caused by the moving film are determined. Traction is the force generated when two surfaces under EHL contact conditions are moving at different speeds. Under full-film lubrication, the traction force is due to the lubricant's resistance to shearing action.

In most mechanical systems, it is desirable to have a fluid with the lowest possible traction properties. These systems are those in which significant sliding occurs between the contact surfaces, for example; tooth-to-tooth contacts in gears, valve train cam and follower contacts, and piston rings. Resistance to sliding results in energy losses and heat generation within the contacts. Lowering the traction will obviously reduce these effects.

In some mechanical systems, a high traction fluid is desirable. A good example is the traction drive. Instead of transmitting power through gears, it is possible to transmit power across a heavily-loaded contact between two rotating disks or rollers. The maximum force, and therefore power that can be transmitted is directly related to the traction force developed in the EHL contact. Higher traction fluids can transmit more power and reduce the amount of sliding between the driven and driving disks. Another component, in which low traction may not be desirable is roller bearings. In this case, some traction is required to reduce the amount of skidding that can take place between the rollers and the bearing raceways.

The traction force is a function of the following parameters: load; lubricant properties; temperature; slip and speed between surfaces; shape of the surfaces; and elastic properties of the contact materials.

Figure 5:
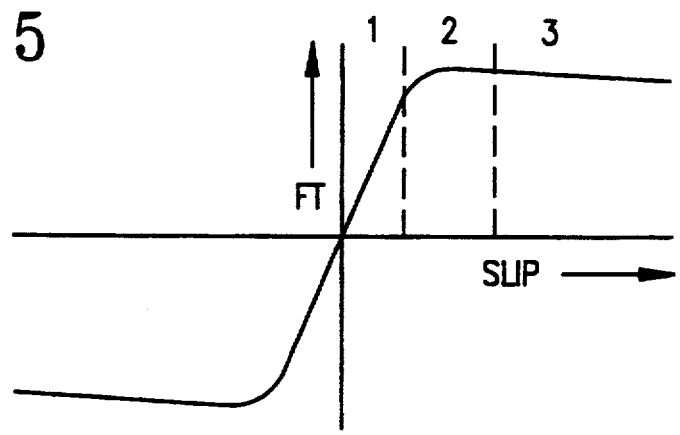
FIG. 5 represents a graph of a generic traction curve.

If the traction force $F_t$ is measured as a function of slip rate, an S-shaped curve as shown in FIG. 5 is generated. This curve can be divided into three regions. At low slip rates (region I in FIG. 5), $F_t$ increases linearly with slip (I). Traction drives and roller bearings operate in this region. In the next region, $F_t$ still increases with S (slip) but not linearly (region II). At higher slip rates (region III), the $F_t$ has reached the limiting shear stress, and $F_t$ slowly decreases as S increases. Worm gears operate on this part of the curve.

The traction force in an EHL contact can be represented as follows:

$$F_t = \int \tau_t dA$$

where A is the contact area that is determined by the shape and elastic properties of the surfaces and $\tau_t$ the shear stress at any given point in the contact. The stress can be related to the shear strain. A general model for this has been proposed and appears below. This model is discussed by J. L. Tevaarwerk and K. L. Johnson in "The Influence of Fluid Reology On The Performance of Traction Drives", Transactions of the ASME, Vol. 101, 266–273, July 1979.

$$\tau_t = G(p,t,T)\mu_s(x) \text{ with } \mu_s(x) = \frac{S \cdot U \cdot (x+a)}{h}$$

At small strains, G is assumed constant for a given p, T (Temperature in fraction) and t (Time). This results in the linear portion of the traction curve.

At higher slip rates, $\tau_t$ reaches a maximum $\tau_{max}$ $F_t$ stabilizes, which accounts for the horizontal part of the traction curve. "F" is the contact. At higher slip rates, heat generation in the contact lowers $\tau_{max}$, resulting in a lower $F_t$.

These forces are measured by strain or force gauges. In order to obtain accurate measurements, as shown in FIG. 1, one part of the measuring structure is supported on base plate 32 while the other is located on frictionless pad 36. Traction force transfer structure 92 is affixed to load plate 100 which in turn is supported on frictionless pad 36. Traction forces ($F_t$) gauge is seated on top of traction force gauge support 96 which is affixed to base plate 32. Traction force gauge support 96, as shown in FIG. 1 has an alignment micrometer 22 positioned therein so as to adjust the forces between support 96 and traction force transfer structure 92. Traction forces generated from the rotating ring and roller, are transferred through load plate 100 without a substantial reduction in the force because of frictionless pad 36. This force is imported through the traction force transfer structure to traction force gauge 98 where it is converted to an electrical signal for machine readability.

Similarly, side force ($F_s$) is obtained by side force strain gauge 102 which is connected by wire to the supporting structure for the roller servo-motor 20 that is affixed to load plate 100. Side force strain gauge 102 is affixed to a structure which is positioned on load plate 100. Therefore, any side movement of the roller servo-motor structure located on load plate 100 above frictionless pad 36 is detected by side force strain gauge 102. Prior to measuring any side movement of roller servo-motor 20, alignment means 12 is used to make certain that the proper alignment exists between frictionless pad 36 and roller servo-motor 20 along its x-axis.

Frictionless pad 36 or a thrust hydrostatic bearing for use here comprises either air or oil as a lubricant. Air gives the best friction characteristics, but is susceptible to contamination by the test fluid or other debris. Special precautions must be taken to avoid this. A hydrostatic air bearing is preferred for use as a frictionless pad.

Air bearing pads can be manufactured to almost any dimensions. A skirt can be fitted around the top half to avoid contamination of the air gap. An air system is likely to give less problems in combination with optical equipment than an oil system. The frictionless pad or air bearing pad utilized herein was custom built to required specifications. Vacuum pre-loading of the bearing avoids excessive air gap fluctuation if the load is varied.

Fluid or gas hydrostatic bearings provide support for systems suspended on load plate 100 while providing for movement in two directions. This allows for easy measurement of both $F_t$ and $F_s$.

Lubricants which can be tested herein include Lube oils, lubricating fluids, semi-solid lubricants, and greases. These lubricants can be manufactured with either a natural or a synthetic base. The amount of lubricant required will generally be less than about one cubic centimeter. This lubricant should be evenly dispersed on the roller when the roller support assembly contains one roller. As is depicted in FIG. 1, multiple rollers are shown. However, it is preferred to use only one roller which will have a diameter less than the inside diameter of ring assembly 19 where it is positioned prior to the lubricant being tested for film thickness and elastohydrodynamic lubricant contact qualities.

The roller which is used herein must be capable of withstanding a speed of 3,000 rpm, be capable of fitting into a ring having an inside diameter of about 50 to 100 mm. Any roller support utilized must not bend or distort the roller. This support must allow the roller to obtain a speed of up to 20,000 rpm. A roller speed of 500 to 3,000 rpm is preferred. Also, roller support 62 must not touch the surface where contact is made with the ring. The roller has an alignment means (not shown) which causes the roller to contact the ring evenly along the internal surface of ring assembly 18.

In order to contact the roller in roller support assembly 26 with ring assembly 18, ring assembly 26 is affixed to roller drive servo 20 which servo is connected to belt drive 28. This belt drive is connected to an electric motor which supplies power to rotate the roller.

Figure 6:
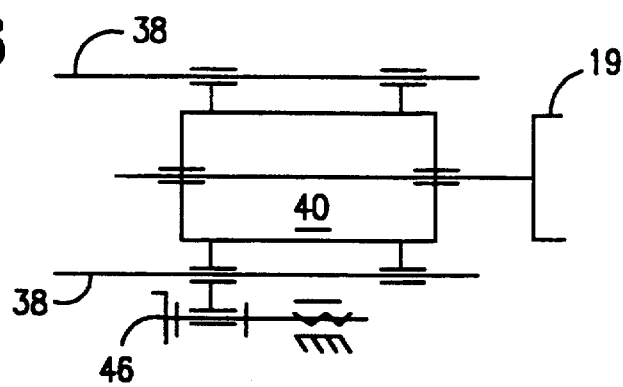
FIG. 6 is a schematic representation of the ring assembly, the spindle/ring positioning means, rails, and positioning screw spindle.
Figure 7:
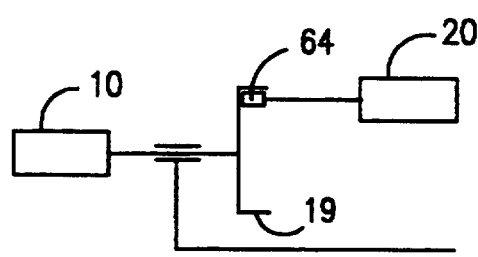
FIG. 7 is a schematic representation of the ring assembly and ring assembly rotating means which is positioned to contact the ring with the roller which has a rotating means connected thereto.

Contact is made between ring assembly 18 and the roller on roller support assembly 26 containing the roller by a linear roller bearing means between rail guides 42 as is shown in FIGS. 6 and 7. These linear roller bearing units are positioned above rails 38 (FIG. 1) affixed to the top of base plate 32 having base levelers 44 located therebelow. Rails 38 are fitted between rail guides 42 which guides are contained on spindle/ring positioning mechanism 40. Spindle unit 14 and spindle sideway assembly 16 are attached centrally on spindle/ring positioning mechanism 40 protruding somewhat over its anterior edge which faces test roller assembly 26.

Figure 8:
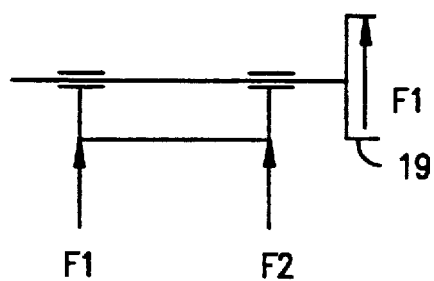
FIG. 8 is a schematic representation of the forces acting on the ring support.

By use of rails and linear roller bearing units, ring assembly 18 can be accurately positioned and preloaded to avoid movement of the ring. As shown in FIG. 8, forces ($F_1$ and $F_2$) on spindle/ring positioning mechanism 40 will point down if $F_1 = 0$ to support the weight of ring assembly 18. As $F_1$, is increased, $F_2$ begins to point up. For this reason, positioning mechanism 40 must have substantially no clearance in the vertical direction as to avoid movement of the ring as $F_1$ is increased i.e. the weight increase caused by extending ring assembly 18 further from spindle sideway assembly 16. In addition to moving ring assembly 18 away from roller 64, the rail and roller bearing unit combination allows for easy cleaning and replacement of parts.

Accurate positioning is only necessary in the area where the ring and roller are in contact. Positioning screw-spindle 46 is then used in that range of ring positioning. When the ring and roller are not in contact with each other, screw spindle 46 is disengaged, thus allowing free movement of spindle/ring assembly 40 on positioning rails 38.

Base plate 32 on which positioning rails 38 are affixed can be made from bolted steel, welded steel, cast iron plate, concrete, or granite. A cast iron base plate is preferred. Cast iron affords maximum flexibility for adding mounting holes for any equipment required to be added later.

Ring assembly 18 includes a ring 19 and a ring holder. The ring holder can be made of ferrous materials. These ferrous materials include carbon steel and stainless steel. Stainless steel is preferred, specifically stainless steel 440. Titanium can also be used.

The transparent ring can be made from either sapphire, HBK 7 tempered glass or Pyrex ® borosilicate glass. Because ring assembly 18 has to operate over a large temperature range i.e., from about −20° C. to about 120° C. the thermal expansion coefficients of the ring and holder must be close to each other to avoid excessive stresses in the ring when run at extreme temperatures. To avoid these stresses, sapphire was selected for the ring. The sapphire ring is bond to a stainless steel holder by an adhesive. This is necessary because sapphire has a high thermal expansion coefficient. To obtain a compressive stress in the bond at all operating temperatures, adhesive, preferably an eopxy adhesive, is applied at or above the maximum operating temperature.

Obviously, many other variations and modifications of this invention as previously set forth may be made without departing from the spirit and scope of this invention as those skilled in the art readily understand. Such variations and modifications are considered part of this invention and within the purview and scope of the appended claims.

What is claimed is:

1. A method for measuring EHL film thickness and traction of a lubricant comprising:
   a) placing a test lubricant onto a roller affixed to a roller assembly which assembly is supported on a moveable base which roller has a first rotating means and a means for rotating said roller affixed thereto, and where said roller assembly also contains a means for loading said roller;
   b) positioning a transparent ring, affixed to a ring assembly which ring has a larger diameter than said roller, over said roller in a manner to contact an internal surface of said ring with the external surface of said roller which ring is affixed to a second rotating means where said ring and second rotating means are affixed to a fixed base which supports a frictionless pad;
   c) causing a transparent heating or cooling chamber to be formed when said ring assembly and roller assembly are positioned together as in step b) which chamber is used to maintain a desired temperature therein thereby heating or cooling said ring and roller;
   d) adjusting the temperature in said heating chamber to a desired temperature;
   e) placing a predetermined load onto said roller via said means for loading said roller;
   f) rotating the ring to a desired speed via said second rotating means while said roller is rotated to another desired speed by said first rotating means;
   g) generating a traction curve by varying the speed of the ring and roller while measuring traction forces created by a lubricant film therebetween; and
   h) measuring the EHL thickness of said film with optical interferometry while viewing said film through said transparent ring.

2. The method as recited in claim 1 where in step e) said load is from about 10 lbs. to about 300 lbs.

3. The method as recited in claim 1 where in step f) the speed of the rotating ring and roller is varied from about 500 rpm to about 3,000 rpm.

4. The method as recited in claim 1 where in step b) said transparent ring is comprised of sapphire tempered glass, or borosilicate glass.

5. The method as recited in claim 1 wherein step d) the temperature is varied while in step e) the load is varied and in step g) the speed is varied sequentially.

6. The method as recited in claim 1 step d) where the temperature of from about −20° to about 120° C.

7. The method as recited in claim 1 step a) where said roller is an elongated cylinder with two raised surfaces thereon sufficient to contact the internal surface of the ring in step b).

8. The method as recited in claim 1 where by changing the shape of the roller a circular, elliptical or linear contact can be formed with said ring and lubricant.

9. The method as recited in claim 1 where in step a) said roller is metal and said ring is sapphire.

10. The method as recited in claim 1 step c) said chamber comprises a transparent plastic material.

11. The method as recited in claim 1 step c) where said chamber is heated with air.

12. The method as recited in claim 1 step g) where a traction force is measured by a traction force cell affixed to the frictionless base when any generated normal forces move it into contact with a stationary support means affixed to the base which supports said frictionless base.

13. The method as recited in claim 1 step d) where said load is placed on said roller via a loading arm adjustably affixed to a servo-motor.

14. The method as recited in claim 1 step g) where any side force generated by the roller assembly rotating means supported on the moveable base is detected by a side force cell which is connected to the fixed base.

15. The method as recited in claim 1 step b) where said ring assembly is affixed to a movable base having a roller bearing means thereunder so as to cause it to move smoothly along rails affixed to the fixed base.

16. The method as recited in claim 1 step a) where said roller is an elongated cylinder supported by two elongated cylindrical rollers meshably interconnected with and under said roller to obtain and maintain proper alignment while said roller is rotating under load.

17. The method as recited in claim 1 step b) where said immovable fixed base is made of cast iron which base has leveling legs positioned thereunder.

18. The method as recited in claim 1 step a) where a metal circumferential enclosure is placed around said roller assembly means in a manner sufficient to allow the roller to rotate without interference where said enclosure forms a foremost minor portion of the heating or cooling chamber in step c).

19. The method as recited in claim 1 step d) where heat in said chamber is determined by a thermocouple sensing means.

20. The method as recited in claim 1 where in step b) the ring assembly has a ring holder to contain said ring which ring holder is made of titanium, carbon steel or stainless steel.

21. The method as recited in claim 1 where in step b) said moveable base and in step b) said fixed base are made of cast iron, bolted steel, welded steel, concrete, or granite.

22. An apparatus for measuring EHL film thickness and traction of a lubricant comprising:
   a) a fixed base sufficient to support a ring assembly and ring assembly rotating means, traction force measuring means, a frictionless support means, a roller assembly and roller assembly rotating means, a loading means, and an optical film measurement means;
   b) a ring assembly and ring assembly rotating means which is slideably affixed to and supported on one end of said base which ring assembly contains a transparent ring;
   c) a frictionless pad position on the opposite end of said base which is sufficient to support a second moveable base smaller than the first base so as to enable said second base to freely move on said first base when traction forces are applied thereto;
   d) a traction force directing means that is affixed to said second base;
   e) a traction force measuring means attached to one side of said fixed base and positioned so that it is able to communicate any traction forces received from the traction force directing means;
   f) a loading assembly means affixed on an end of the second base so as to be remote from but in line with the ring assembly means which loading assembly means has a load pivoting means with a lever arm attached thereto;
   g) a pivotal roller assembly means positioned in front of the load pivoting means so as to transfer applied forces via said lever arm to at least one roller located in the roller assembly and supported by two free wheeling roller supports which supports rotate when the roller, connected to a roller rotating means, rotates;
   h) a cylindrical lid fitted around said roller assembly means in a manner sufficient to form a heating or cooling chamber when a transparent cylinder open at one end and enclosingly fitted around the ring assembly at the other end is slideably positioned over said ring assembly and into said lid;
   i) a side force transferring means which is affixed to a side of the second base and which communicates with a side force measuring means that is attached to said fixed base, and
   j) an optical measurement means which is attached to said fixed base in a manner sufficient to allow optical interference measurements from a lubricant film between the rotating roller and a rotating transparent ring affixed to said ring assembly.

23. The apparatus as recited in claim 22 where in step f) said lever arm can support a load from about 10 lbs. to about 300 lbs.

24. The apparatus as recited in claim 22 where in steps b) and g) the ring and roller are rotated at a speed from about 500 rpm to about 3,000 rpm.

25. The apparatus as recited in claim 22 where in step b) said transparent ring is comprised of sapphire, tempered glass, or borosilicate glass.

26. The apparatus as recited in claim 22 wherein step h) said heat chamber allows the temperature to vary while in step f) a load on the lever arm is varied and in steps b) and g) the ring and roller rotating speed are varied sequentially.

27. The apparatus as recited in claim 22 step h) where the chamber is sufficient to allow heating to a temperature of from about 30° to about 120° C.

28. The apparatus as recited in claim 22 step g) where said roller is an elongated cylinder with two raised surfaces thereon sufficient to contact the internal surface of the ring in step b).

29. The apparatus as recited in claim 22 whereby changing the shape of the roller a circular, elliptical or linear contact can be formed with said ring and lubricant.

30. The method as recited in claim 22 where in steps b) and g) said roller is metal and said ring is sapphire.

31. The apparatus as recited in claim 22 step h) said chamber comprises a transparent plastic material.

32. The apparatus as recited in claim 22 step h) where said chamber is heated with air.

33. The apparatus as recited in claim 22 step e) where a traction force is measured by a side-force cell affixed to the frictionless pad when any generated normal forces move it into contact with a stationary support means affixed to the fixed base which supports said frictionless pad.

34. The apparatus as recited in claim 22 step f) where a load is placed on said roller via a lever arm adjustably affixed to a servo-motor.

35. The apparatus as recited in claim 22 step g) where any side force generated by a roller assembly rotating means supported on a second moveable base is detected by a side force cell which is connected to the fixed base.

36. The apparatus as recited in claim 22 step b) where said ring assembly is affixed to a slideable base having a roller bearing means thereunder so as to cause it to move smoothly along rails affixed to the fixed base.

37. The apparatus as recited in claim 22 step g) where said roller is an elongated cylinder supported by two elongated cylindrical rollers meshably interconnected with and under said roller to obtain and maintain proper alignment while said roller is rotating under load.

38. The apparatus as recited in claim 22 step b) where said fixed base is made of cast iron which base has leveling legs positioned thereunder.

39. The apparatus as recited in claim 22 step g) where a metal circumferential enclosure or lid means is place around said roller assembly means in an manner sufficient to allow the roller to rotate without interference where said enclosure forms a foremost minor portion of the chamber in step h).

40. The apparatus as recited in claim 22 step h) where heat in said chamber is determined by a thermocouple sensing means.

41. The apparatus as recited in claim 22 where in step b) the ring assembly has a ring holder to contain said ring which ring holder is made of titanium, carbon steel or stainless steel.

42. The apparatus as recited in claim 22 where in step a) the fixed base and in step c) said moveable second base is made of cast iron, bolted steel, welded steel, concrete, or granite.

43. The apparatus as recited in claim 22 where in step g) said roller comprises a metal ball.

44. The apparatus as recited in claim 22 where in steps b) and g)) said ring and roller respectively are made from steel, bronze, tungsten carbide, and ceramic materials, or combinations and mixtures thereof.

* * * * *